United States Patent [19]

Selin

[11] 4,003,917
[45] Jan. 18, 1977

[54] SILOXANEDIOLATE COMPLEXES AND PREPARATION THEREOF

[75] Inventor: Terry G. Selin, Schenectady, N.Y.

[73] Assignee: General Electric Company, Waterford, N.Y.

[22] Filed: May 27, 1975

[21] Appl. No.: 581,146

Related U.S. Application Data

[62] Division of Ser. No. 602,490, Dec. 19, 1966, Pat. No. 3,923,834.

[52] U.S. Cl. ............... 260/340.6; 260/448.2 E
[51] Int. Cl.² ................................. C07D 319/10
[58] Field of Search ..................... 260/340.6

[56] References Cited

UNITED STATES PATENTS 3,018,160   1/1962   Miller ..................... 260/340.6

*Primary Examiner*—Ethel G. Love
*Attorney, Agent, or Firm*—Donald J. Voss; E. Philip Koltos; Frank L. Neuhauser

[57] ABSTRACT

Siloxanediolate/p-dioxane complexes and processes for preparing the complexes. Sodium or an amalgam thereof is reacted with arylsilicondiols in the presence of p-dioxane to form the complexes. Complexes are useful in preparing the corresponding aryl polysiloxanediols.

7 Claims, No Drawings

SILOXANEDIOLATE COMPLEXES AND PREPARATION THEREOF

This application is a division of copending application Ser. No. 602,490, filed Dec. 19, 1966, now U.S. Pat. No. 3,923,834.

This invention relates to novel siloxanediolate/p-dioxane complexes, and to processes for preparing the complexes.

For some time, efficient processes have been available for the production of disiloxanediols such as tetraphenyldisiloxane-1,3-diol, commonly referred to as "dimerdiol." In sharp contrast, only inefficient and cumbersome processes have been available for the production of related "trimerdiols" such as hexaphenyltrisiloxane-1,5-diol. The present invention has to do with processes for preparing trimerdiols of excellent purity in high yield, and particularly has to do with new siloxanediolate complexes from which the trimerdiols can be so prepared.

It is an object of this invention, therefore, to provide novel siloxanediolate/p-dioxane complexes.

Another object is to provide processes for preparing the complexes.

Still another object is to provide processes for preparing polysiloxanediols.

Additional objects of the invention will be apparent from the following description.

In accordance with the present invention, there are provided siloxanediolate complexes having the general formula

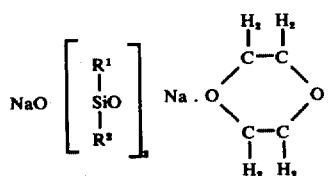

(1)

wherein $R^1$ and $R^2$ are aryl radicals.

In accordance with the present invention, there are also provided processes for preparing the complexes, particularly by reacting sodium or an amalgam thereof with an arylsilicondiol having the general formula

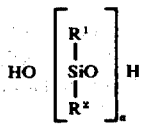

(2)

wherein $R^1$ and $R^2$ are ad defined above, and $a$ is an integer of 1 or 2, in the presence of p-dioxane.

Another embodiment of the invention comprises a process for forming aromatic polysiloxanediols having the general formula

(3)

wherein $R^1$ and $R^2$ are aryl radicals which comprises: acidifying a siloxanediolate complex with a weak or dilute acid.

In the complexes of general formula (1), $R_1$ and $R_2$ represent any conventional aryl radical. Included among these aryl radicals are both unsubstituted aryl radicals and aryl radicals which contain substituents which are generally inert under the reaction conditions involved in the present invention. Typical unsubstituted aryl radicals include, for example, phenyl, naphthyl, and biphenyl radicals. Typical substituted radicals include tolyl, xylyl, ethylphenyl, phenoxphenyl, p-chlorophenyl, o-bromophenyl, p-cyanophenyl, p-nitrophenyl, trifluoromethylphenyl, and n-trimethylsilyphenyl radicals.

Representative of the complexes of general formula (1) are:

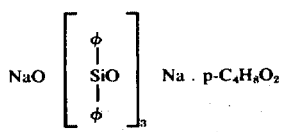

and

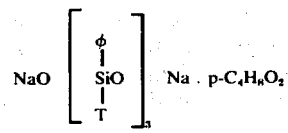

wherein $\phi$ represents phenyl, T represents p-tolyl, and $p\text{-}C_4H_8O_2$ represents p-dioxane.

The preferred process for forming the complexes of general formula (1) comprises reacting sodium or an amalgam thereof in dioxane with an arylsilanediol having the general formula

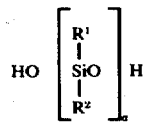

(2)

wherein $R^1$ and $R^2$ are as defined above, and $a$ is 1 or 2. Typical diols include: diphenylsilanediol; tetraphenyldisiloxane 1,3-diol; phenyl p-tolyl silanediol; and tetrakis-(p-chlorophenyl)-disiloxanediol.

As is apparent from the foregoing description of the present invention, either an arylsilanediol or an aryldisiloxanediol is reacted with sodium in the presence of p-dioxane to form a complex which is a trisiloxane. This conversion of the silane or the disiloxane to a trisiloxane complex is completely unexpected and could not have been predicted from a knowledge of the art. While the mechanism of the reaction is not known, it can be postulated that when the diol is a silanediol, three molecules of the silanediol condense to form the trisiloxane and then the complex. No simple explanation is available for the conversion of the disiloxanediol to the trisiloxane complex, but the reaction probably involves both a condensation and a rearrangement. In any event, regardless of whether the starting material within the scope of formula (2) is a silane or a disiloxane, the principal product of the reaction is the trisiloxane complex of formula (1).

As indicated above, sodium or an amalgam thereof is reacted with a diol of general formula (2) in the presence of p-dioxane to form the desired complex. Generally, an excess of sodium is used in order to insure formation of the desired diolate. As a guide, therefore, from about 0.67 to about 3 equivalents of sodium is employed for each hydroxyl group of the diol employed.

When an individual diol is reacted with sodium in keeping with this invention, a diolate complex is formed in the following manner. Diphenylsilanediol and sodium are used for illustrative purposes:

$$p\text{-}C_4H_8O_2 + 3 \text{ HOSiOH} + 4 \text{ Na} \longrightarrow \text{NaO} \begin{bmatrix} \phi \\ | \\ \text{SiO} \\ | \\ \phi \end{bmatrix}_3 \text{Na} \cdot p\text{-}C_4H_8O_2 + 2 \text{ NaOH} + 2\text{H}_2$$

(where the diol bears $\phi$ groups)

p-Dioxane appears to be unique in having a capacity to form the complexes of general formula (1). Opposed to the behavior of p-dioxane is that of simple ethers such as diethyl ether. With the latter, complicated mixtures are obtained as products rather than complexes. The mixtures contain silanolates, silanols and cyclic siloxanes. Correspondingly, ethylene glycol dimethyl ether and N-methyl-morpholine failed to form the desired complexes when used in the same manner as p-dioxane.

While p-dioxane can be used as a reactant in forming the complexes of general formula (1), it can also be used as a solvent for the reactants. Other materials, however, can also be used as solvents, included among which are: hydrocarbons — benzene, toluene and xylenes.

Reaction of sodium with a diol of general formula (2) is conducted at a temperature of from about 10° C to about 100° C and preferably 30° to 60° C when the p-dioxane is used both as a reactant and a solvent. However, when the p-dioxane is used as a reactant and a higher boiling hydrocarbon is used as a solvent, the reaction temperature can be increased to as high as the boiling point of the hydrocarbon solvent, which can range up to 150° to 175° or 180° C, depending upon the particular hydrocarbon solvent employed. With p-dioxane as both the reactant material and the solvent, reaction time will generally range from about 1 to about 8 hours, with the 10° to 100° C reaction temperature range. On the other hand, when higher reaction temperatures are employed, the reaction rate is increased accordingly, with the broad reaction temperature range being from about 0.25 hour up to about 8 hours.

The actual manipulative technique for effecting the reaction between the sodium, the diol and the p-dioxane is relatively straightforward. A solution is formed in an appropriate reaction vessel of the diol and the p-dioxane and any additional solvent which may be used in the reaction. The resulting reaction mixture is then maintained at the reaction temperature while particles of finely divided sodium are slowly added. The reaction mixture is agitated constantly, and completion of the reaction is evidenced by the fact that hydrogen evolution ceases. Once the reaction has been completed, the reaction mixture consists of particles of unreacted sodium, a fine suspension of the desired complex of formula (1), and a liquid phase. The reaction mixture is roughly filtered to remove sodium and then the suspended complex is filtered from the reaction mixture and dried under a stream of inert gas to yield the desired complex.

In addition to the preferred process described above for forming the complexes of general formula (1), several other processes have been developed. A metal silanolate having the general formula $$\text{Na} \begin{bmatrix} R^3 \\ | \\ \text{OSi}-R^4 \\ | \\ R^5 \end{bmatrix} \quad (4)$$

wherein $R^3$–$R^5$ are hydrocarbyl radicals, can be reacted with a cyclic polysiloxane having the general formula $$\begin{bmatrix} R^1 \\ | \\ \text{SiO} \\ | \\ R^2 \end{bmatrix}_b \quad (5)$$

in the presence of p-dioxane, wherein $b$ is an integer of at least 3, e.g. from 3 to 7, or more.

Hydrocarbyl groups, $R^3$–$R^5$, include: alkyl — methyl, ethyl, propyl, isobutyl, n-butyl, sec-butyl and octyl; olefinically unsaturated monovalent hydrocarbon radicals — vinyl, allyl and cyclohexenyl; aryl — phenyl, tolyl, xylyl, naphthyl and diphenyl; aralkyl — benzyl and phenylethyl; cycloalkyl — cyclohexyl and cycloheptyl.

Suitable silanolates for this process include: sodium trimethylsilanolate; sodium triethylsilanolate; sodium triphenylsilanolate; and sodium dimethylphenylsilanolate.

Polysiloxanes of general formula (5) are also well known. Typical reactants of this class include: octaphenylcyclotetrasiloxane; hexaphenylcyclotrisiloxane and sym-pentaphenylpenta-m-tolylcyclopentasiloxane.

Reaction of a silanolate of general formula (4) with a cyclic polysiloxane of general formula (5) is carried out at a temperature ranging from about 10° C. to about 150° C. or more. Molar proportions of the silanolate and polysiloxane can be varied from about 2:1 to about 5:1. Here again, dioxane can be employed alone as the reaction medium or can be used as a reactant together with a hydrocarbon solvent.

Another process for forming the desired complexes involves reaction of a disilanolate having the general formula

$$\text{NaO} \begin{bmatrix} R^3 \\ | \\ SiO \\ | \\ R^4 \end{bmatrix}_a \text{Na} \quad (6)$$

with a cyclic polysiloxane having the general formula

$$\begin{bmatrix} R^1 \\ | \\ SiO \\ | \\ R^2 \end{bmatrix}_b \quad (5)$$

in the presence of p-dioxane, wherein $R^1$–$R^4$, $a$ and $b$ are as defined above.

Representative disiloxane diolates include: disodium tetramethyldisiloxanediolate; disodium diphenyldisiloxanediolate, and disodium tetraphenyldisiloxanediolate.

Reaction conditions employed in reacting a disilanolate with a cyclic polysiloxane are the same as for the corresponding reaction with a monosilanolate.

A related modification involves reaction of a cyclic polysiloxane with a metal siloxanolate having the general formula

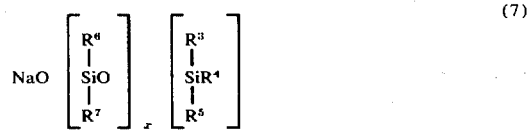

$$\text{NaO} \begin{bmatrix} R^6 \\ | \\ SiO \\ | \\ R^7 \end{bmatrix}_x \begin{bmatrix} R^3 \\ | \\ SiR^4 \\ | \\ R^5 \end{bmatrix} \quad (7)$$

wherein $R^3$ through and inclusive of $R^7$ are hydrocarbyl radicals, and $x$ is an integer of at least 1, in the presence of p-dioxane. Here too, reaction conditions are the same as those employed with a monosilanolate and the polysiloxane. Typical disiloxanolates include sodium: 1,1,1-trimethyl-3, 3-diphenyldisiloxan-3-olate; 1,1,1,3-tetramethyl-3-beta-cyanoethyldisiloxan-3-olate and 1,1,1-trimethyl-3-vinyl-3-vinyl-3-methyldisiloxan-3-olate.

Still another process for forming the desired complexes involves reaction of a metal alkoxide having the general formula $$\text{NaOr}^3 \quad 8.$$

wherein $R^3$ is a hydrocarbyl group, with a cyclic polysiloxane of general formula (5) in the presence of p-dioxane. Suitable alkoxides include sodium methoxide, sodium ethoxide, sodium propoxide, and sodium phenoxide.

An additional process for preparing the desired complexes is that of reacting sodium hydroxide with a cyclic polysiloxane of general formula (5) in the presence of p-dioxane.

In all of the processes involving sodium hydroxide, sodium silanolates and sodium alkoxides, the general reaction procedure is similar in that the sodium-free polysiloxane together with the p-dioxane and any other solvent which is to be employed are added to a reaction vessel and maintained at a reaction temperature in the range of from about 10° to 100° or 150° C and the sodium-containing material is added. The reaction mixture is maintained at this temperature until the reaction is completed, at which time the reaction mixture consists of a liquid phase having a suspension of the desired complex of formula (1). This complex is then filtered from the reaction mixture, washed with a hydrocarbon solvent, and then dried under an inert gas to produce the complex in substantially pure form.

An important feature of the present invention is the preparation of aryl polysiloxanediols having the general formula

$$\text{HO} \begin{bmatrix} R^1 \\ | \\ SiO \\ | \\ R^2 \end{bmatrix}_a \text{H} \quad (3)$$

by acidifying and decomposing a siloxanediolate complex of general formula (1) with a weak or dilute acid. Thus, the acid should have a hydrogen ion concentration of less than about 2 molar. Greater hydrogen ion concentrations tend to cause condensation of the desired products (diols), thereby leading to the formation of unwanted products.

The acidification can take place in either dilute solutions of strong acids or in concentrated solutions of weak acids. For example, acid solutions with the proper hydrogen ion concentration can be obtained by using dilute solutions of mineral acids, such as hydrochloric acid or sulfuric acid. On the other hand, glacial acetic acid is satisfactory in the process without dilution, since the hydrogen ion concentration of glacial acetic acid is not greater than the two molar maximum desired in the process.

Temperatures employed for acidification range from about 20° C to about 150° C, dependent upon acid strength. The more dilute the acid, the higher the temperature may be; and with less dilute acids, lower temperatures of the 20°–150° C. range are employed.

In order to convert the complex to the desired trisiloxanediol of formula (3), the complex is merely added to the acid medium where the acid causes decomposition of the complex with the liberation of p-dioxane and the diolate of the trisiloxane which almost instantly is converted to the desired diol. The amount of acid employed for the acidification is not critical, with the only requirement being that there is sufficient acid present so as to be able to manipulate the reaction mixture and so that there is sufficient acid present to neutralize and acidity the complex.

Where mineral acids are employed for the acidification, the acid will be present as an aqueous solution having the hydrogen ion concentration no greater than 2 molar. This dilute acid is generally mixed with at least an equal volume of a suitable solvent for the trisiloxanediol of formula (3) so that the diol will be readily dissolved and so that purification of the diol will be facilitated. The complex is added to the mixture of the aqueous acid and the solvent which is preferably diethyl ether or an aromatic solvent, such as benzene, toluene, xylene, or the like. The mixture is agitated to insure thorough contact of each of the phases with the other and with the complex. After the decomposition and neutralization is effected, a two-phase solution results with the trisiloxanediol in the organic phase and with the salts resulting from the neutralization in the aqueous phase. The phases are separated, the organic phase is washed with water to remove residual acid, and the solvent is evaporated to produce the solid trisiloxanediol.

Where neutralization is effected in an organic acid such as glacial acetic acid, the complex is merely added to the glacial acetic acid and the reaction mixture is agitated. The resulting mixture is slowly added to an excess of water and the trisiloxanediol precipitates from the reaction mixture and is isolated by filtration.

The invention is illustrated, and in no sense limited, by the following examples. Unless indicated otherwise, all parts are by weight.

EXAMPLE 1

Disodium hexaphenyltrisiloxane-1,5-diolate, p-dioxane complex was formed by the procedure given below:

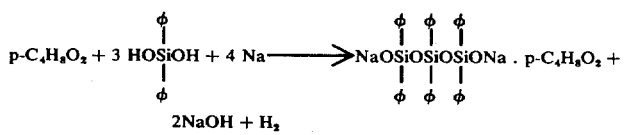

2NaOH + H$_2$

In a 1 liter flask 108 g. (0.5 mole) of $\phi_2$Si (OH)$_2$ was dissolved in 400 ml. of dry dioxane. A reflux condenser was attached to the flask. The system was then swept with dry nitrogen and then placed under a blanket of nitrogen for the duration of the reaction. To the resulting solution was added 30 g. of freshly cut sodium in the form of approximately 1 g. chunks. The mixture was stirred by means of a magnetic stirrer as hydrogen evolution began immediately. During the first 3 hours the temperature of the mixture rose to 55° C, with precipitation of a fine white product. The mixture was stirred for an additional 3 hours and then allowed to stand at room temperature overnight. The excess sodium was then removed by filtering the reaction mixture through a wire screen which allowed the fine crystalline product to pass onto a regular filter paper where it was retained. Thus isolated, the diolate complex was washed with a little fresh dioxane, then dried under a stream of nitrogen. The resulting white solid was a fine powder with melting point 206° – 228° C (decomposition). Upon titration of the material with standard acid, it was found to contain 6.22% Na compared to the theoretical value of 6.20% Na for the structure NaO ($\phi_2$SiO)$_3$Na·C$_4$H$_8$O$_2$. Further evidence for the 1:1 character of the complex was a 13.7% weight loss upon heating at 210° C under a vacuum to constant weight. This compares favorably with the theoretical value of 11.9% for removal of one dioxane molecule in a 1:1 complex. Further structure proof is indicated by its infrared spectrum and its conversion to hexaphenyltrisiloxane-1,5-diol (see Example 5 below).

EXAMPLE 2

Tetraphenyldisiloxane-1,3-diol was used in place of diphenylsilanediol under the condition described in EXAMPLE 1. A 96% yield of the desired p-dioxane complex was obtained, in accordance with the following equation:

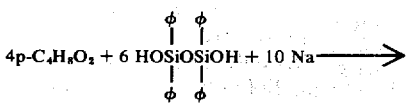

-continued

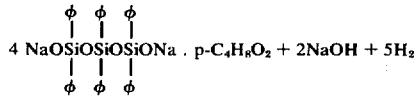

EXAMPLE 3

The procedure of EXAMPLE 1 was repeated with 3% sodium amalgam in place of sodium metal. The same complex was obtained in a yield of about 85%.

EXAMPLE 4

This example illustrates the use of a solvent other than dioxane. Excess sodium was added to a solution of 43.2 g. (0.2 mole) of $\phi_2$Si (OH)$_2$ and 100 g. of p-dioxane in 200 ml. of dry benzene. The resulting mixture was stirred under a blanket of nitrogen for about 3 hours. (maximum reaction temperature of 54° C) then refluxed for an additional 3 hours. The resulting milkline mixture was cooled and worked up as in EXAMPLE 1. This yielded 45 g. (91%) of the trisiloxanediolate complex whose infrared spectrum was identical with that obtained from the product in EXAMPLE 1.

EXAMPLE 5

Hexaphenyltrisiloxane-1,5-diol was prepared from the corresponding complex, as indicated below:

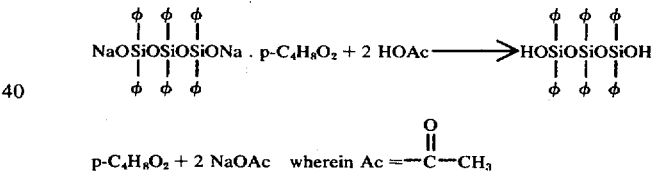

To a mixture of 300 ml. of ethyl ether and 600 ml. of 5% aqueous acetic acid in a separatory funnel was added 60 g. of Na (OSi$\phi_2$)$_3$ONa·C$_4$H$_8$O$_2$. The mixture was agitated well at 25° C and the ether layer isolated. The ether layer was washed twice with water and then dried briefly over anhydrous sodium sulfate. Removal of the ether solvent by flash evaporation yielded 42 g. (85%) of a viscous liquid which upon standing crystallized completely. The crystalline material was shown to be pure hexaphenyltrisiloxane-1,5-diol by infrared and melting point (110°–113° C) comparison with a reference sample. The melting point was improved to 112°–113° C by a single recrystallization from a hexane-benzene mixture.

As will be apparent from the foregoing illustrative material, the new complexes are useful intermediates for example, for the preparation of corresponding aryl polysiloxanediols. Furthermore, polysiloxanediols such as trimerdiol are useful as silicone rubber process aids (plasticizers), such as illustrated in U.S. Pat. No. 2,890,188 – Konkle et al.

The foregoing examples and discussion are intended to illustrate a number of embodiments of the invention. It is to be understood, however, that the invention relates broadly to the complexes as new compositions of matter, to processes for forming the complexes, and to processes in which the complexes are converted to related products. Thus, the scope of the invention is defined by the appended claims taken together with the foregoing description.

I claim:

1. A process for forming a siloxanediolate complex having the formula

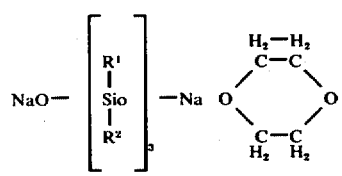

which comprises: reacting a metalsilanolate having the general formula

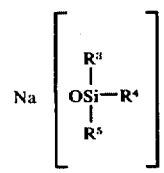

wherein $R^3$, $R^4$, and $R^5$ are hydrocarbyl radicals, with a cyclic polysiloxane having the general formula

in the presence of p-dioxane, where $b$ is an integer of at least 3 and $R^1$, $R^2$ are aryl radicals.

2. The process of claim 1, wherein the silanolate is sodium trimethylsilanolate.

3. The process of claim 1, wherein the polysiloxane is octaphenyltetrasiloxane.

4. A process for forming a siloxanediolate complex having the formula

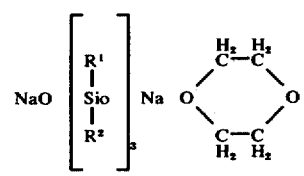

which comprises: reacting a disilanolate having the general formula

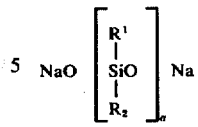

wherein $o$ is 1 or 2, with a cyclic polysiloxane having the general formula

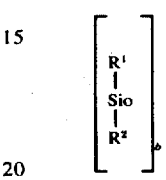

in the presence of p-dioxane, where $b$ is an integer of at least 3 and $R^1$, $R^2$ are aryl radicals.

5. A process for forming a siloxanediolate complex having the formula

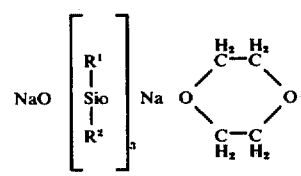

which comprises: reacting a metal siloxanolate having the general formula

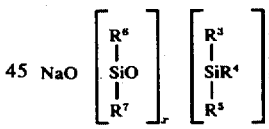

wherein $R^3$ through and inclusive of $R^7$ are hydrocarbyl radicals and $x$ is an integer of at least 1, with a cyclic polysiloxane having the general formula

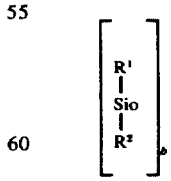

in the presence of p-dioxane, where $b$ is an integer of at least 3, wherein $R^1$, $R^2$ are aryl radicals.

6. A process for forming a siloxanediolate complex having the formula

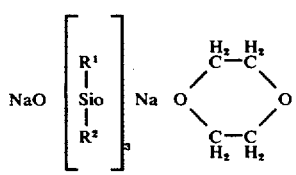

which comprises: reacting a metal alkoxide having the general formula

NaOR³ wherein R³ is a hydrocarbyl group, with a cyclic polysiloxane having the general formula

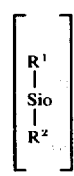

in the presence of p-dioxane, where $b$ is an integer of at least 3, wherein R¹, R² are aryl radicals.

7. A process for forming a siloxanediolate complex having the formula

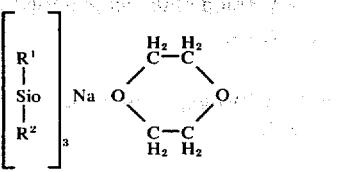

which comprises: reacting sodium hydroxide with a cyclic polysiloxane having the general formula

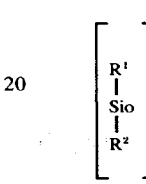

in the presence of p-dioxane, where $b$ is an integer equal to at least 3, wherein R¹, R² are aryl radicals.

* * * * *